Figure 1:
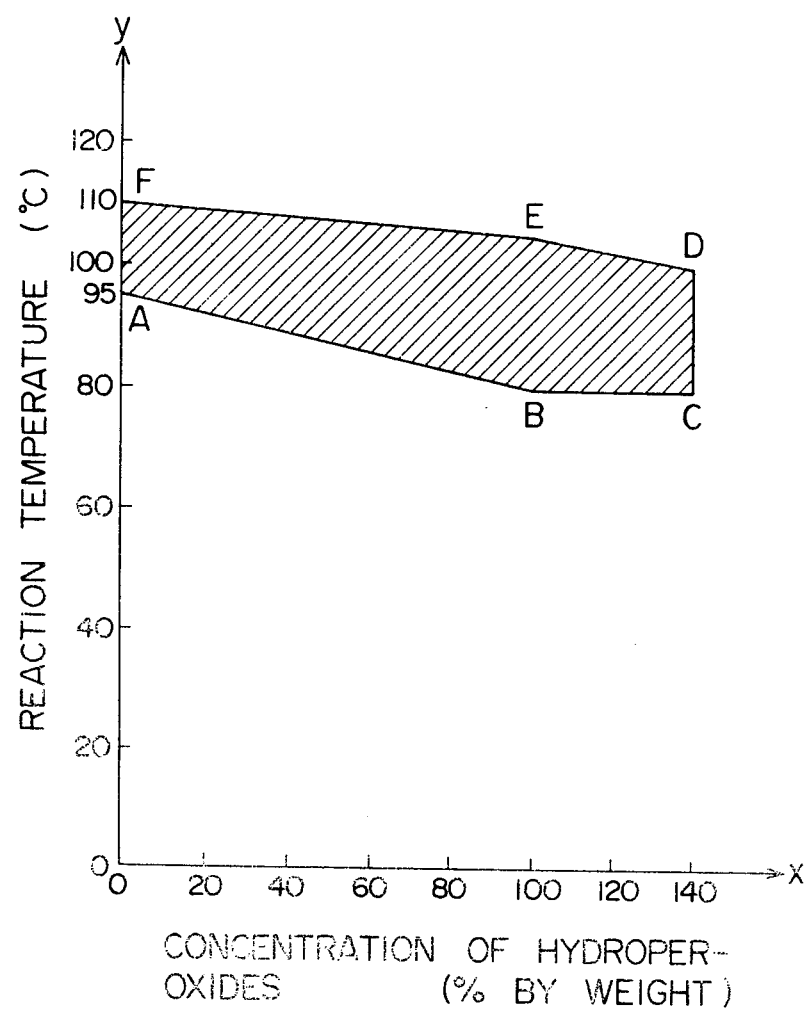

United States Patent [19]

Nambu et al.

[11] 4,237,319
[45] Dec. 2, 1980

[54] PROCESS FOR LIQUID-PHASE OXIDATION OF M-DIISOPROPYLBENZENE

[75] Inventors: Hirohiko Nambu, Ohtake; Isao Hashimoto, Waki; Ichiro Imai, Ohtake, all of Japan

[73] Assignee: Mitsui Petrochemical Industries Ltd., Tokyo, Japan

[21] Appl. No.: 954,072

[22] Filed: Oct. 24, 1978

[30] Foreign Application Priority Data

Oct. 31, 1977 [JP] Japan .................. 52/129664

[51] Int. Cl.³ ............... C07C 179/035; C07C 177/047
[52] U.S. Cl. ................................................ 568/571
[58] Field of Search ............... 568/571, 573, 574, 572

[56] References Cited

U.S. PATENT DOCUMENTS

| 2,715,646 | 8/1955 | Hawkins et al. | 568/573 |
| 2,796,439 | 6/1957 | Berneis | 568/573 |

*Primary Examiner*—Werren B. Lone
*Attorney, Agent, or Firm*—Sherman & Shalloway

[57] ABSTRACT

A process for producing m-diisopropylbenzene dihydroperoxide which comprises oxidizing m-diisopropylbenzene in the liquid phase with molecular oxygen under alkaline conditions; wherein the oxidation is carried out under conditions (A), (B) and (C) below, (A) under conditions which meet (i), (ii), (iii) and (iv) below,
(i) $0 \leq x \leq 140$
(ii) $y \geq 80$
(iii) $-0.05x + 110 \geq y \geq -0.15x + 95$ wherein $0 \leq x \leq 100$
(iv) $y \leq -0.25x + 130$ wherein $100 < x \leq 140$ in which x represents the absolute value of the concentration of hydroperoxides in the oxidation product in % by weight calculated as m-diisopropylbenzene monohydroperoxide, and y represents the absolute value of the reaction temperature in degrees centigrade, (B) until x reaches at least 120, and
(C) so that the reaction temperature at $100 < x \leq 140$ is lower than the reaction temperature at the start of the reaction (x=0).

7 Claims, 2 Drawing Figures

PROCESS FOR LIQUID-PHASE OXIDATION OF M-DIISOPROPYLBENZENE

BACKGROUND OF THE INVENTION

Field of the Invention

This invention relates to an improved process for the liquid-phase oxidation of m-diisopropylbenzene (to be referred to as m-DIPB) which can afford in a high yield within a shortened period an oxidation product containing a major proportion of m-diisopropylbenzene dihydroperoxide (to be referred to as m-DHP) and a minor proportion of 2-hydroxy-2-propyl-$\alpha,\alpha$-dimethylbenzyl hydroperoxide (to be referred to as m-HHp) and di-(2-hydroxy-2-propyl)benzene (to be referred to as m-DC) which are convertible to m-DHP.

A process for producing resorcinol is known which comprises oxidizing m-DIPB in the liquid phase with molecular oxygen under alkaline conditions to form m-DHP, separating a fraction containing a major proportion of m-DHP from the resulting m-DHP-containing oxidation product, and cleaving the separated fraction with an acid. It has been the conventional practice in the performance of this process to isolate m-DHP having the highest possible purity from the oxidation product and subjecting the resultant m-DHP to acid-cleavage. In order to obtain m-DHP of high purity, the liquid-phase oxidation in accordance with the prior art is carried out under such conditions as will inhibit the formation of oxidation by-products other than m-DHP and m-diisopropylbenzene monohydroperoxide (to be referred to as m-MHP), such as m-HHP and m-DC which are not easily separable. Specifically, the oxidation reaction is not advanced to a great extent, but is stopped at a relatively early stage so as to inhibit the formation of the oxidation by-products, and to limit the concentrations of hydroperoxides in the reaction system.

However, it is operationally complicated and difficult to separate high purity m-DHP from such oxidation by-products which are difficult to separate, and no procedure which can perform such separation effectively has yet been provided. For this reason, separation of m-DHP from the oxidation product in the prior art causes various troubles. For example, the inclusion of by-products such as m-HHP or M-DC, or partial decomposition of m-DHP cannot be avoided. Such a process has therefore not proved to be entirely satisfactory when it is desired to obtain resorcinol in a high yield by cleaving the separated m-DHP with acids.

The present inventors noted that m-HHP and m-DC, the formation of which are avoided in the conventional liquid-phase oxidation of m-DIPB with molecular oxygen, can be easily converted to m-DHP by an oxidizing agent, preferably hydrogen peroxide, and thought that if an oxidation product containing a major proportion of m-DHP and a minor proportion of m-HHP and m-DC can be formed, it would be possible to avoid the troubles of the prior techniques which require the separation of m-DHP in a high purity. This gave incentive to a study of developing such an improved process.

As a result, the present inventors found that by performing the oxidation reaction under specified conditions to a high degree contrary to the conventional practice, the total yield of m-DHP, m-HHP and m-DC can be increased within a shortened period and an m-DHP-rich oxidation product can be formed, thus making it possible to overcome the troubles of the prior art advantageously.

It has also been found that since m-HHP and m-DC can be easily converted to m-DHP by oxidation with an oxidizing agent, the inclusion of a step of oxidizing the oxidation reaction product with an oxidizing agent can afford m-DHP in an increased yield and can provide a commercially advantageous process for producing m-DHP.

It is an object of this invention therefore to provide an improved process for the liquid-phase oxidation of m-diisopropylbenzene.

The above and other objects and advantages of the invention will become more apparent from the following description.

According to this invention, there is provided a process for producing m-diisopropylbenzene dihydroperoxide which comprises oxidizing m-diisopropylbenzene in the liquid phase with molecular oxygen under alkaline conditions, wherein the oxidation is carried out under conditions (A), (B) and (C) below, (A) under conditions which meet (i), (ii), (iii) and (iv) below,
  (i) $0 \leq x \leq 140$
  (ii) $y \geq 80$
  (iii) $-0.05x + 110 \geq y \geq -0.15x + 95$
    wherein $0 \leq x \leq 100$
  (iv) $y \leq -0.25x + 130$
    wherein $100 < x \leq 140$
in which x represents the absolute value of the concentration of hydroperoxides in the oxidation product in % by weight calculated as m-diisopropylbenzene monohydroperoxide, and y represents the absolute value of the reaction temperature in degrees centigrade, (B) until x reaches at least 120, preferably at least 130, and (C) so that the reaction temperature at $100 < x \leq 140$ is lower, preferably at least about 3° C. lower, than the reaction temperature at the start of the reaction ($x = 0$).

The concentration (x % by weight) of hydroperoxides in the oxidation product is determined by iodometrically analyzing a water-free sample of the oxidation product for hydroperoxide groups, and calculating the amount of hydroperoxides as m-MHP.

The liquid-phase oxidation of m-DIPB with molecular oxygen is carried out under alkaline conditions. Usually, the reaction is carried out in the presence of an aqueous solution of an alkali, and preferably under such alkaline conditions that the pH of the oil layer (determined by collecting a sample from the oil layer, shaking it together with water in the same volume as the sample, and then measuring the pH of water) is 7 to 11, especially about 8 to about 10. If the pH of the oil layer is on the acid side, it is difficult to increase the concentrations of the hydroperoxides in the oxidation product. If the pH of the oil layer is too high, the amounts of by-products increase. To maintain the pH of the oil layer within the above range, it is preferred to maintain the pH of the alkaline aqueous solution at at least about 9, especially at more than about 10 but less than about 12, although this varies, for example, depending upon the stirred condition of the reaction system. The concentration of the alkaline aqueous solution is preferably not more than about 20% by weight because too high concentrations are likely to result in the migration of a part of the resulting m-DHP to the aqueous layer by dissolution.

Examples of suitable alkalis include sodium hydroxide, potassium hydroxide, sodium carbonate and potassium carbonate. The amount of the aqueous alkali solution may be varied properly according to the concentration, the type of the alkali, etc. For example, when a 5% by weight aqueous solution of sodium hydroxide is used, its amount is preferably about 8 to about 50% by weight, more preferably about 12 to about 40% by weight, based on the entire liquid phase of the reaction system.

Since the liquid-phase oxidation reaction is carried out using molecular oxygen under alkaline conditions, it is advisable to operate the process such that m-DIPB, alkali and molecular oxygen will come into full contact with one another. To aid in obtaining full contact of the liquid phase, the aqueous alkali solution (aqueous layer) and molecular oxygen, for example oxygen or an oxygen-containing gas such as air or a gaseous mixture in optional proportions of oxygen and nitrogen or another inert gas, it is possible to employ a means of mechanical stirring, a means of circulating a part of the liquid phase in the reaction system into the reaction zone by a pump, a means of stirring the reaction system by blowing oxygen or an oxygen-containing gas, or an optional combination of these means.

The reaction pressure that can be employed is atmospheric pressure to about 10 kg/cm$^2$.

It is first essential to perform the liquid-phase oxidation in this invention under conditions (A). Conditions (A) will be described with reference to FIG. 1, which is a graphic representation showing the relation between the reaction temperature and the concentration of hydroperoxides in the oxidation product specified in conditions (A). In this Figure, line AB represents $y = -0.15x + 95$; line BC, $y = 80$; line CD, $x = 140$; line DE, $y = -0.25x + 130$; and line EF, $y = -0.05x + 110$. Accordingly, the hatched area surrounded by these straight lines meets (i) to (iv) specified in conditions (A). In the process of this invention, the reaction is performed within this area.

To increase the total yield of m-DHP, m-HHP and m-DC and the content of m-DHP within as short a period as possible, the liquid-phase oxidation must be performed under conditions (B) and (C) in conjunction with condition (A).

If y is smaller than line AB or BC in FIG. 1 (namely, the reaction temperature is lower), the rate of the reaction is extremely low. In this case, too, m-DHP, m-HHP and m-DC can be obtained in more or less good yields by sufficiently prolonging the reaction time; but it is undesirable because the content of m-DHP decreases. On the other hand, if y is larger than line DE or EF (namely, the reaction temperature is higher), the rate of the reaction is high, but vigorous decomposition of the resulting hydroperoxides occurs, and markedly reduces both the total yield of m-DHP, m-HHP and m-DC and the content of m-DHP. The content of m-DHP decreases abruptly in a region in which the concentration (x) of hydroperoxides in the oxidation product exceeds 140% by weight.

The liquid-phase oxidation in accordance with this invention must also be carried out until the concentration (x % by weight) of hydroperoxides at the end of the reaction reaches at least 120% by weight, preferably at least 130% by weight [condition (B)]. In other words, x at the end of the reaction is $120 \leq x \leq 140$, preferably $130 \leq x \leq 140$. When the reaction is stopped before x reaches 120, the content of m-MHP or m-DIPB in the oxidation reaction product increases markedly. Use of such an oxidation product cannot afford resorcinol in a high yield. The reaction should not be carried out until x exceeds 140 because it will abruptly decrease the content of m-DHP.

In addition to the conditions (A) and (B), the process of this invention should also meet condition (C) under which the liquid-phase oxidation reaction should be carried out so that the reaction temperature at $100 < x \leq 140$ is lower (preferably at least 3° C. lower, more preferably at least about 5° C. lower) than the reaction temperature at the initiation of the reaction (x = 0).

The employment of the reaction temperature meeting the condition (C) in addition to the conditions (A) and (B) makes it possible for the first time to increase both the total yield of m-DHP, m-HHP and m-DC and the content of m-DHP. Usually, the suitable temperature ranges from the reaction temperature at x = 0 to a temperature about 25° C., preferably about 10°–15° C., lower than it. It is especially preferred that the reaction temperature at $120 \leq x \leq 140$ be adjusted to about 85° C. to about 95° C. The reaction temperature can be lowered at a fixed rate or in a multiple of stages. Alternatively, the oxidation may be performed at a fixed temperature, then the temperature lowered within a short period (for example, within 1 hour), and then the oxidation continued.

The mode of the liquid-phase oxidation may be any desired one. For example, it may be performed batchwise or continuously.

After performing the liquid-phase oxidation reaction under the specified conditions (A), (B) and (C), the reaction mixture is separated into an aqueous layer and an oil layer by, for example, allowing it to stand. The aqueous layer is removed, and the oil layer is recovered to obtain an oxidation product containing m-DHP as a major ingredient and m-HHP and m-DC as minor ingredients in a good yield. The resulting oxidation product can be used as a material for acid-cleavage either as such or after separating m-DHP. In the most preferred embodiment of this invention, the oxidation product is further oxidized with an oxidizing agent to convert m-HHP and m-DC to m-DHP, and the resulting product may be used as a starting material in a known acid-cleavage step.

Hydrogen peroxide and an organic peroxide such as peracetic acid, ketone hydroperoxide or ketone peroxide can be used as the oxidizing agent in this additional oxidation step. The use of hydrogen peroxide is most preferred in view of the operation of separating the product and the efficiency of oxidation.

Preferably, the additional oxidation by an oxidizing agent is carried out by using hydrogen peroxide in the form of an aqueous solution, diluting the oxidation product obtained by the action of molecular oxygen and alkali with an aromatic hydrocarbon, and performing the reaction in the presence of an acid catalyst in the heterogeneous system. The amount of hydrogen peroxide used at this time is generally about 0.5 to about 20 equivalents, preferably about 2 to about 15 equivalents, per equivalent of alcoholic hydroxyl group of m-HHP and m-DC of the oxidation product. Sulfuric acid, perchloric acid and phosphoric acid, for example, can be used as the acid catalyst.

Preferably, the reaction of the oxidation product with hydrogen peroxide is carried out under conditions which will not cause the decomposition of m-DHP.

Suitable conditions may be employed by properly controlling the reaction temperature, the amount of the acid catalyst, the amount of water, etc.

The reaction temperature in the additional oxidation reaction is preferably about 20° to about 70° C., more preferably about 30° to about 60° C. The amount of the acid catalyst differs according to the type of the catalyst, but for example, it is about 0.5 to about 5 moles/liter of the aqueous layer. The preferred amount of water is such that the concentration of hydrogen peroxide is about 1 to about 15 moles/liter.

After the additional oxidation by oxidizing agents, the product is separated into two layers. The aqueous layer is removed, and the oil layer is recovered to obtain the oxidation product.

The oxidation product obtained by the process of this invention, preferably after additional oxidation with an oxidizing agent, can be utilized for the production of resorcinol by acid-cleavage in a manner known per se.

The acid-cleavage reaction can be carried out by applying any of the methods heretofore used in the acid cleavage reaction of the oxidation product of diisopropylbenzenes. For example, the oxidation product after contact with hydrogen peroxide may be contacted with an acid catalyst after optionally distilling off a part or the whole of the aromatic hydrocarbon and optionally adding another solvent. Examples of the acid catalyst that can be used in the acid-cleaving reaction of the oxidation product are inorganic acids such as sulfuric acid, perchloric acid and phosphoric acid, organic acids such as chloroacetic acid or p-toluenesulfonic acid; and solid acids such as cation exchange resins, silica-alumina and silica-titania.

When an inorganic acid or an organic acid is used as the acid catalyst, the reaction system is preferably homogeneous. For this purpose, a solvent which dissolves both the oxidation reaction product and the acid catalyst, for example a ketone such as acetone, methyl ethyl ketone, diethyl ketone or methyl isobutyl ketone, can be used as a reaction solvent.

The amount of the inorganic or organic acid as the acid catalyst is, for example, about 0.1 to about 15% by weight, preferably about 0.2 to about 5% by weight, based on the oxidation product. The acid-cleavage reaction can be performed at a reaction temperature of about 40° to about 100° C., preferably about 50° to about 90° C.

When a solid acid is used as the acid catalyst, the reaction system becomes heterogeneous. In this case, too, the use of the ketone as a reaction solvent is preferred. The solid acid can be used in an amount of about 2 to about 100% by weight, preferably about 20 to about 80% by weight. The acid-cleavage reaction in the presence of solid acid catalysts can be performed at about 40° to about 100° C., preferably about 70° to about 90° C.

Resorcinol can be recovered by treating the reaction mixture after the acid-cleavage reaction in a customary manner. For example, resorcinol can be obtained by distilling off acetone, the solvent, etc. from the reaction mixture after the reaction, and further subjecting the product to distillation, crystallization, extraction, etc.

The process of this invention can afford m-DHP in high yields. In particular, by the additional oxidation with an oxidizing agent, m-DHP of a high concentration with very small amounts of m-HHP and m-DC can be obtained. Thus, it can be used directly as a starting material for acid-cleavage without the need for a step of separating m-DHP as in the prior art processes.

The following Examples and Comparative Examples illustrate the present invention is more detail.

EXAMPLES 1 to 6 AND COMPARATIVE EXAMPLES 1 to 4

A reactor equipped with an air blowing sparger at its bottom and an inlet for introducing an aqueous alkali solution and a reflux condenser at its top was charged with 100 parts by weight of m-DIPB and 5 parts by weight of a 5% aqueous solution of each of the alkalies indicated in Table 1. The inside of the reactor was pressurized with air until the pressure reached each of the values indicated in Table 1, and then, the reaction temperature (in the Examples, the temperatures at $x=0$) was raised as shown in Table 1. Then, while blowing air at a speed of 1.2 cm/sec (in an empty column), m-DIPB was oxidized batchwise at the temperatures and pressures shown in Table 1. Throughout the reaction, the aqueous alkali solution was added intermittently so as to maintain the pH of the oil layer at 9.0 to 11.0. The reaction conditions and the results are shown in Table 1.

TABLE 1

| Example (Ex.) or Comparative Example (CEx.) | Alkali | Pressure (kg/cm$^2$) | Temperature (*1) | Time (hours) (*2) | $x_E$ (%) (*3) | Yield (%) (*4) | m-DHP/ m-HHP + m-DC (weight ratio) |
|---|---|---|---|---|---|---|---|
| Ex. 1 | NaOH | 6.5 | 106° C. at $0 \leq x \leq 80$; then lowered to 93° C. at a rate of 0.5° C./hr | 31 | 135 | 83 | 2.52 |
| Ex. 2 | Na$_2$CO$_3$ | 5.7 | 102° C. at $0 \leq x \leq 80$; then lowered to 92° C. over 1 hour; and the reaction performed at 92° C. | 36 | 133 | 82 | 2.51 |
| Ex. 3 | NaOH | 5.5 | 100° C. at $0 \leq x \leq 90$; then lowered to 90° C. over 2 hours; and the reaction performed at 90° C. | 39 | 136 | 83 | 2.67 |
| Ex. 4 | NaOH | 5.5 | Lowered at a rate of 0.5° C./hr from 107° C. at $x = 0$ to 82° C. at $x = 127$ | 50 | 127 | 79 | 2.56 |
| Ex. 5 | NaOH | 4.6 | 100° C. at $0 \leq x \leq 100$ C.; then lowered to 85° C. at a rate of 0.5° C./hr; and then the reaction performed at 85° C. | 52 | 130 | 81 | 2.69 |
| Ex. 6 | Na$_2$CO$_3$ | 5.5 | Same as in Example 3 | 43 | 135 | 82 | 2.72 |
| CEx. 1 | Na$_2$CO$_3$ | 6.5 | 106° C. | 24 | 113 | 67 | 1.31 |
| CEx. 2 | NaOH | 5.7 | 102° C. | 30 | 121 | 69 | 189 |
| CEx. 3 | NaOH | 5.5 | 100° C. | 34 | 125 | 71 | 1.93 |

TABLE 1-continued

| Example (Ex.) or Comparative Example (CEx.) | Alkali | Reaction conditions Pressure (kg/cm$^2$) | Temperature (*1) | Time (hours) (*2) | $x_E$ (%) (*3) | Yield (%) (*4) | m-DHP/ m-HHP + m-DC (weight ratio) |
|---|---|---|---|---|---|---|---|
| CEx. 4 | NaOH | 4.6 | 85° C. | 82 | 123 | 72 | 1.70 |

(*1): x represents the concentration of hydroperoxides in the oxidation product in % by weight calculated as m-MHP.
(*2): The time from the initiation to the end of the reaction.
(*3): The hydroperoxide concentration at the end of the reaction.
(*4): The total yield of m-DHP, m-HHP and m-DC in mole %.

EXAMPLE 7

Toluene was added to the oxidation product obtained in Example 3. The mixture was washed with water to prepare a hydroperoxide solution having the composition shown in Table 2.

TABLE 2

| Ingredients | Content (% by weight) |
|---|---|
| m-DHP | 17.8 |
| m-HHP | 6.1 |
| m-DC | 0.5 |
| m-MHP | 2.1 |
| Toluene | 71.4 |
| Others | 2.1 |

A reactor equipped with a distillation column and a water-separating device at its top and a stirrer was continuously charged hourly with 100 parts by weight of the hydroperoxide solution shown in Table 2 and 50 parts by weight of an aqueous solution containing 27% by weight of hydrogen peroxide and 12% by weight of sulfuric acid, and they were reacted at a reaction pressure of 160 mmHg and a reaction temperature of 50° C. with vigorous stirring with an average residence time of 10 minutes. The aqueous layer in the distillates at the top was continuously withdrawn out of the reaction system at a speed of 3 parts by weight per hour. The remainder of the aqueous layer, and the toluene layer were returned to the reaction system. The reaction mixture was continuously withdrawn out of the system and separated into an oil layer and an aqueous layer. An analysis of the oil layer showed that m-HHP and m-DC had been converted to m-DHP in a conversion of 98% and 95%, respectively.

What we claim is:

1. In a process for producing m-diisopropylbenzene dihydroperoxide by oxidizing m-diisopropylbenzene in the liquid phase with molecular oxygen under alkaline conditions at a pressure of from atmospheric pressure to about 10 kg/cm$^2$; the improvement comprising carrying out the oxidation reaction at a reaction temperature y in the range of from 80° C. to 110° C. until the concentration x of hydroperoxides in the oxidation product, in percent by weight, calculated as m-diisopropylbenzene monohydroperoxide, reaches at least 120 but not more than 140, while maintaining the relationship between x and y within the shaded area $\overline{ABCDEF}$ shown in FIG. 1, and lowering the reaction temperature by at least about 3° C. from the initial reaction temperature (when x=0) when x becomes greater than 100.

2. The process of claim 1 wherein the oxidation is carried out until x reaches at least 130.

3. The process of claim 1 wherein the resulting oxidation product is further oxidized with an oxidizing agent.

4. The process of claim 3 wherein the oxidizing agent is an organic peroxide.

5. The process of claim 3 wherein the oxidizing agent is hydrogen peroxide.

6. The process of claim 1 wherein the reaction is conducted at a pressure from atmospheric to about 10 kg/cm$^2$.

7. The process of claim 1 wherein the oxidation reaction temperature when x reaches 120 until the end of the oxidation reaction is within the range of from about 85° C. to about 95° C.

* * * * *